United States Patent
Brattesani

[11] Patent Number: 5,587,284
[45] Date of Patent: *Dec. 24, 1996

[54] PERIODONTAL PROBE TIP AND METHOD FOR USING

[76] Inventor: Steven J. Brattesani, 3051 Laguna St., San Francisco, Calif. 94123

[*] Notice: The term of this patent shall not extend beyond the expiration date of Pat. No. 5,423,677.

[21] Appl. No.: 438,685

[22] Filed: May 11, 1995

Related U.S. Application Data

[62] Division of Ser. No. 148,159, Nov. 4, 1993, Pat. No. 5,423,677.

[51] Int. Cl.⁶ .............................. A61C 19/04; A61C 1/00; A61C 3/00; A61C 5/00
[52] U.S. Cl. .............................. 433/72; 433/29; 433/75; 433/215
[58] Field of Search .............................. 433/2, 3, 29, 72, 433/75, 141, 215; 128/776, 777; 33/513, 514

[56] References Cited

U.S. PATENT DOCUMENTS

| | | |
|---|---|---|
| 3,935,640 | 2/1976 | Cohan . |
| 4,203,223 | 5/1980 | Lautenschlager et al. . |
| 4,501,555 | 2/1985 | Ditchburn . |
| 4,768,952 | 9/1988 | Loewenthal . |
| 4,790,751 | 12/1988 | Reinhardt et al. . |
| 4,886,454 | 12/1989 | Loewenthal et al. . |
| 4,995,403 | 2/1991 | Beckman et al. . |
| 5,022,856 | 6/1991 | Zimble . |
| 5,044,951 | 9/1991 | Sheridan . |
| 5,096,240 | 3/1992 | Loewenthal . |
| 5,112,226 | 5/1992 | Lemon et al. . |
| 5,178,537 | 1/1990 | Currie . |
| 5,244,386 | 8/1993 | Angelo, Jr. . |
| 5,271,734 | 12/1993 | Takeuchi . |

FOREIGN PATENT DOCUMENTS 8403143  8/1984  WIPO .

OTHER PUBLICATIONS

Pro–Dentec, Inc., PDT Perioprobe—1993 Trade Literature 1993.
Pro–Dentec, Inc., Sensor Probe—1993 Trade Literature 1993.
Denta–Logic, Inc., Denlite—1993 Trade Literature 1993.
Periodontics: Emerging Computer Technologies in Periodontics, Miller et al., Dentistry Today, p. 6, Sep. 1993.

*Primary Examiner*—Nicholas D. Lucchesi
*Attorney, Agent, or Firm*—John P. O'Banion

[57] ABSTRACT

A translucent periodontal probe tip (10) for measuring the depth of gingival pockets (30) for purposes of diagnosing the progression of periodontal disease. The periodontal probe tip (10) includes color-coded regions (24a, 24b, 24c), corresponding to different stages of periodontal disease, depending on the depth of the gingival pockets (30) of a subject patient. A plurality of numbered graduations (26) are placed among colored regions (24a, 24b, 24c) for purposes of more accurately determining the depth of gingival pockets (30). Periodontal probe tip (10) is capable of being illuminated from a light source (22) which carries light to probe tip (10), thus allowing a dentist to easily read colored regions (24a, 24b, 24c) and graduations (26) placed on the probe tip (10). A method for using probe tip (10) for diagnosing the progression of periodontal disease is also described.

15 Claims, 5 Drawing Sheets

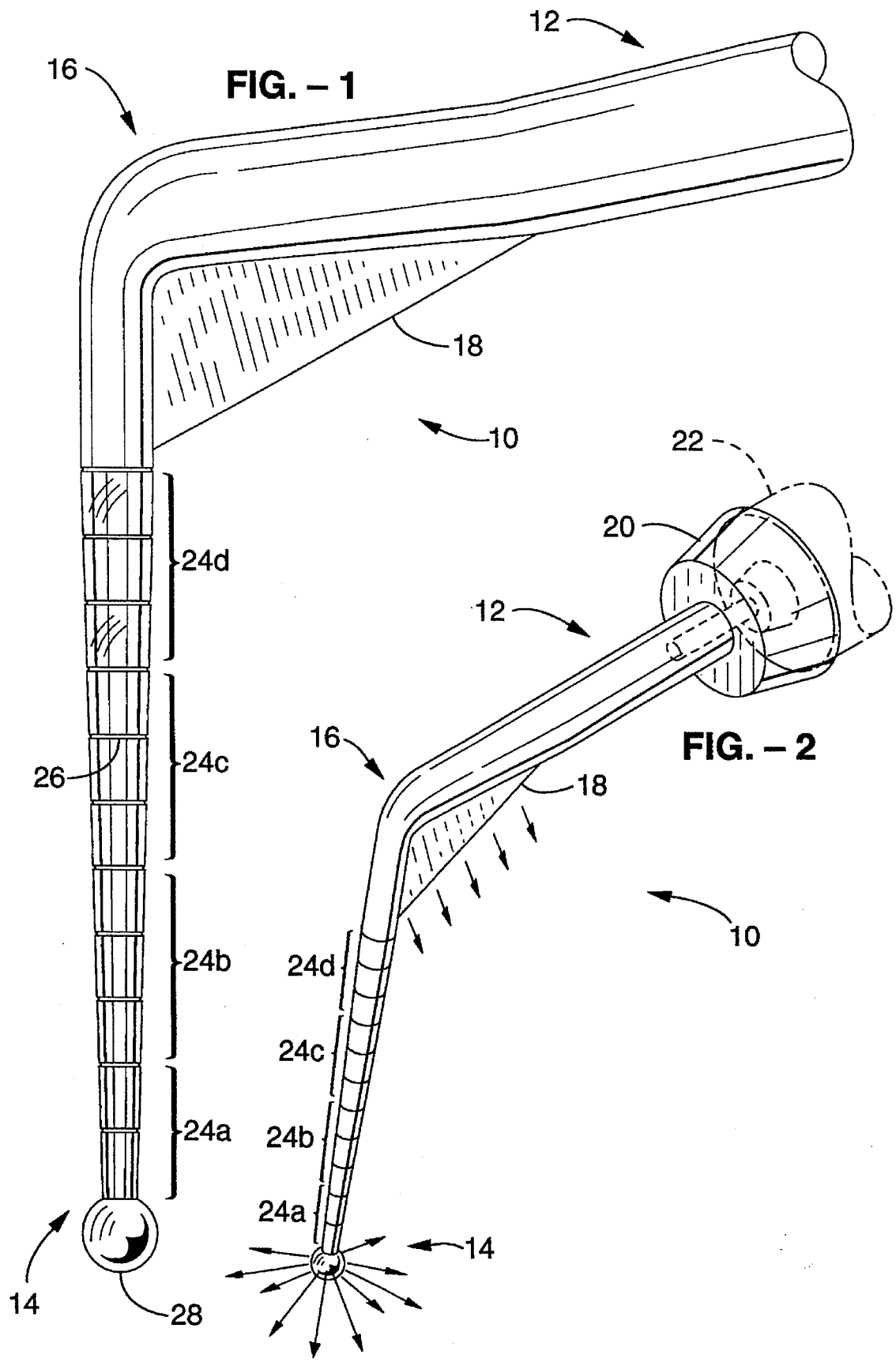

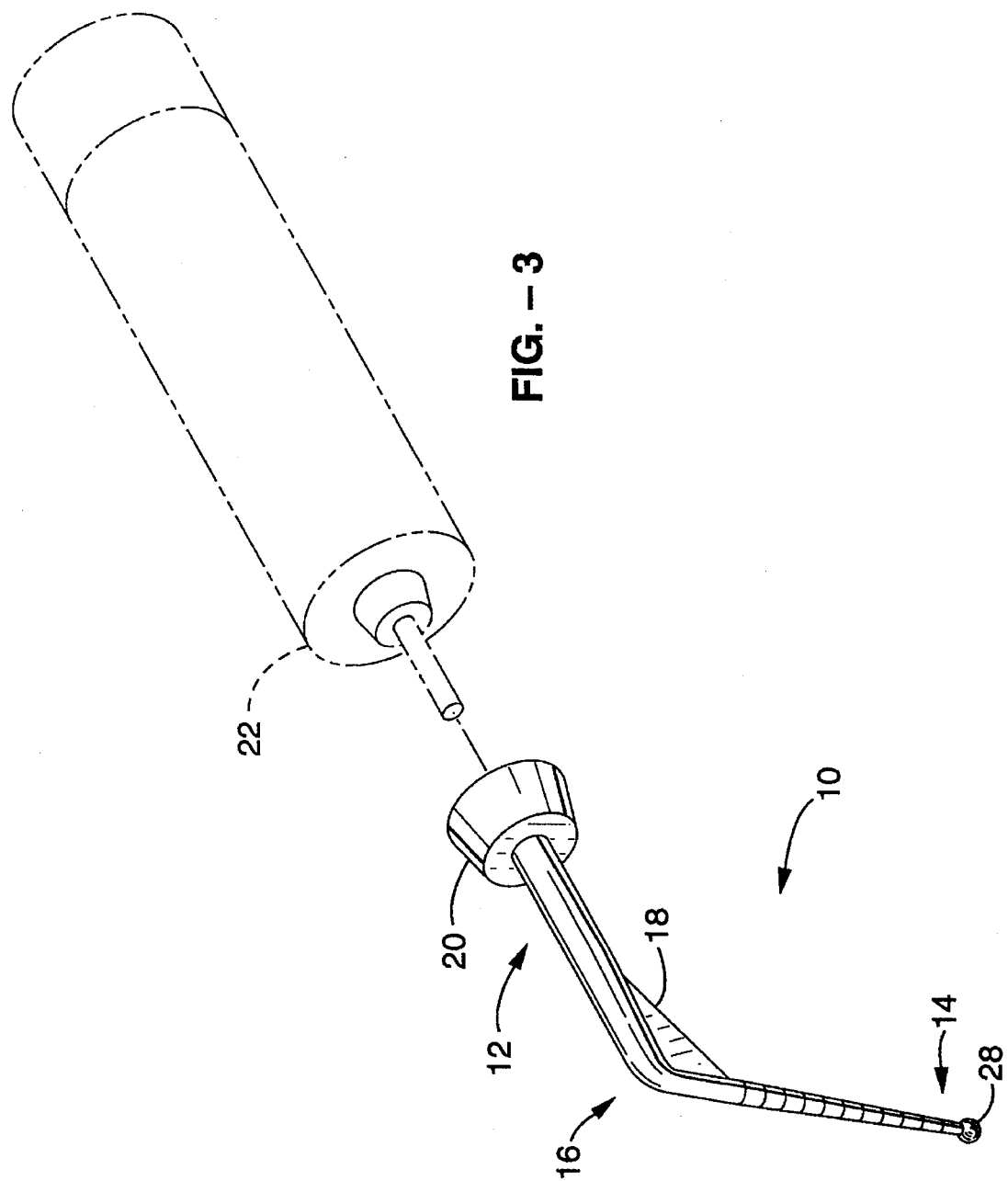

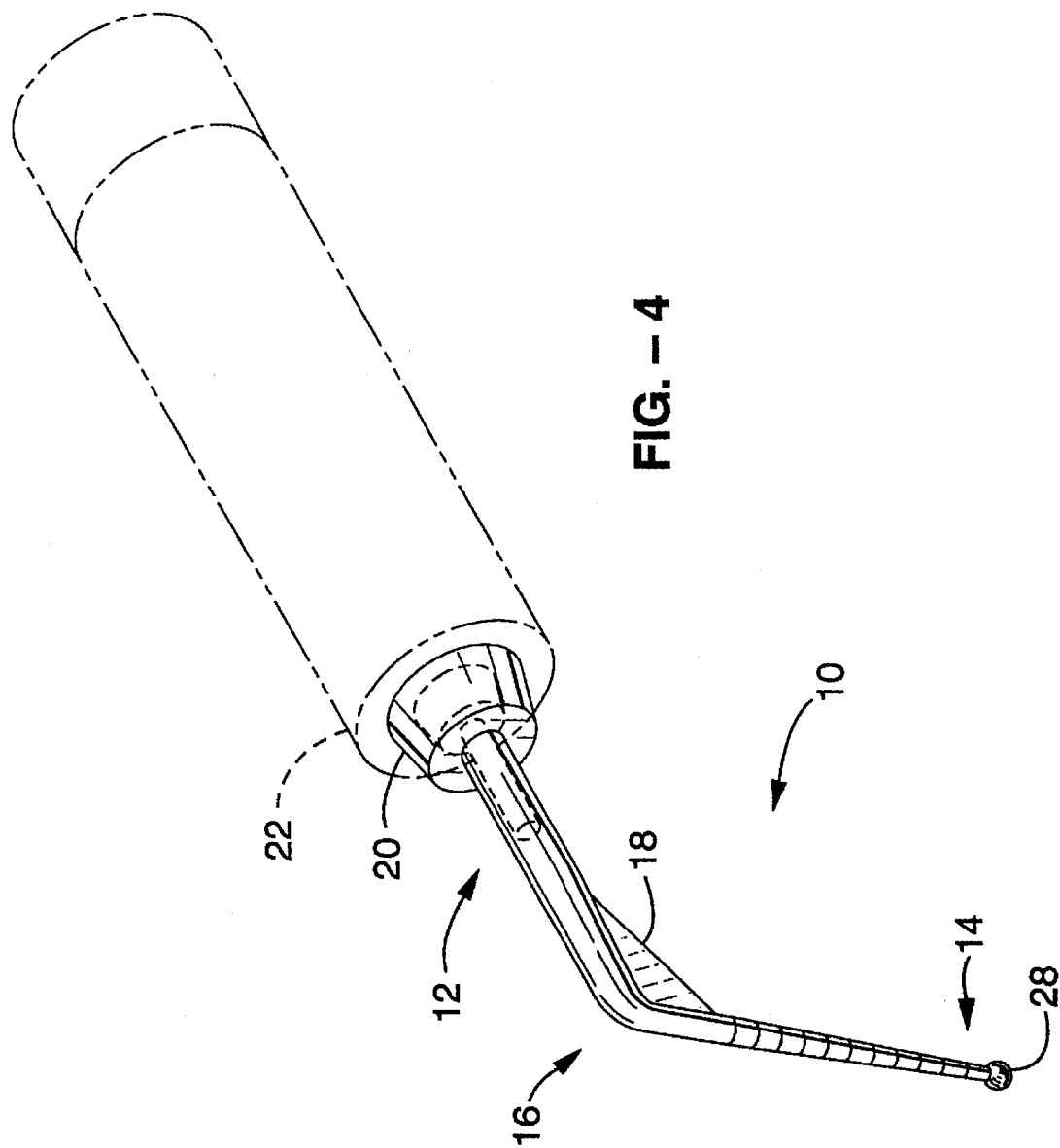
FIG.—4

PERIODONTAL PROBE TIP AND METHOD FOR USING

CROSS REFERENCE TO RELATED APPLICATIONS

This is a divisional of application Ser. No. 08/148,159 filed on Nov. 4, 1993, now U.S. Pat. No. 5,423,677.

BACKGROUND OF THE INVENTION

1. Field of the Invention

This invention pertains to dental appliances generally, and more particularly, to a translucent periodontal probe tip capable of illumination, having color-coded regions for generally determining the level of progression of periodontal disease, and measured graduations placed among the color-coded regions for more carefully determining the level of progression of periodontal disease. A method for using the periodontal probe tip described herein is also presented.

2. Description of the Background Art

Periodontal disease is a common affliction of the mouth characterized by swelling of the gums resulting from the buildup of plaque upon the teeth. In time, periodontal disease can lead to the destruction of the supporting bone of the teeth, which eventually can result in tooth loss.

Early detection of periodontal disease is crucial to preventing tooth loss and the periodontal probe has become the primary weapon used by dentists in the war against periodontal disease. The standard method for diagnosing periodontal disease involves measuring the depth of the periodontal, or gingival, pockets present between the teeth and gums, using a periodontal probe. The standard periodontal probes used to date have either graduations or other marks on the probe tip to indicate the depth which the probe tip penetrates between the tooth and gum. A non-diseased condition is indicated by a probe tip depth of about 1 to 3 millimeters. An insertion of the periodontal probe tip beyond 1 to 3 millimeters indicates that bone loss has occurred, and that preventative steps must be taken to prevent further deterioration of the subject patient's bone and gums.

Other periodontal probe designs have recently incorporated color-coded regions on the probe tip as a time saving measure which allows a dentist to more quickly differentiate healthy teeth from unhealthy teeth. Periodontal probes incorporating color-coding generally have a first green colored region indicating the first "healthy" 1–3 millimeter depth, and a second red colored region indicating an "unhealthy" depth beyond 1–3 millimeters. Additionally, such color-coded probes may also incorporate a band or mark at the border between different colored regions indicating, for example the 3 millimeter point. In using such a periodontal probe, the dentist can insert the probe tip between the teeth and gums and quickly obtain a general indication of a patient's dental health by determining if a particular tooth reads "green" or "red". The dentist can then record which teeth are diseased and which are healthy.

A significant shortcoming of the previously discussed periodontal probes employing graduations and/or color-coding, involves the difficulty encountered by the dentist in reading the color-coding and graduations once the probe is in position between the teeth and gums. Overhead dental lights provide insufficient illumination for the accurate and quick reading of the colors and graduations present on the probe tip of a periodontal probe. A more viable solution has been to employ an illuminated probe tip and hence, periodontal probes incorporating a translucent probe tip, having graduations thereon, as well as an illumination means, have been devised for purposes of measuring gingival pockets. Additionally, periodontal probes using a light beam for measuring gingival pocket depths have been devised. These probes generally use reflected light beams to determine the depth of a pocket wherein the reflected light from the probe end is detected by a computer, which provides an accurate pocket depth measurement. However, such a sophisticated probe employing a computer is expensive and complex.

The periodontal probes previously discussed have not endeavored to provide an illuminated probe incorporating a quick-measure, color-coded feature with a more accurate, graduation-measure, feature. Such a combination of features is highly desirable in that the dentist using the appliance could quickly check a patient's teeth by inserting the illuminated probe tip between a patient's teeth and gums and easily read the color-coding as a first step. If periodontal disease is indicated, the dentist can then advance to a second, more accurate diagnostic step by reading the depth of penetration of the probe as indicated by a plurality of marks or graduations on the probe tip. The desirability of a probe incorporating these features would be further enhanced by incorporating a detachable coupler which would allow the probe tip to be detached and readily disposed of. The detachability feature is highly desirable for purposes of reducing the chance of transmitting communicable diseases, such as Acquired Immune Deficiency Syndrome (AIDS) or hepatitis, as a result of re-using a soiled probe tip. A probe incorporating these features would also be significantly less expensive and complex than periodontal probes incorporating computer measurement means.

The present invention represents a substantial advancement in the design of periodontal probes, which overcomes the deficiencies of the prior art to result in a probe which inexpensively increases dental efficiency in diagnosing periodontal disease.

The foregoing discussion reflects the state of the art of which the applicant is aware and is tendered with the view toward discharging the applicant's acknowledged duty of candor in disclosing information which may be pertinent in the examination of this application. It is respectfully stipulated, however, that none of these previous devices teach or render obvious, singly or when considered in combination, the applicant's claimed invention.

SUMMARY OF THE INVENTION

The present invention pertains to a periodontal probe tip having a probing end constructed from a translucent, light conducting, plastic-like material. Upon coupling the probe tip to a light source, light is conducted to the point of examination within a subject patient's mouth. The periodontal probe tip also incorporates a plurality of adjacent colored regions which indicate varying levels of progression of periodontal disease. Each colored region progressing away from the probing end indicates a deepening penetration of the probe tip and, thereby, indicates a progressively more serious periodontal condition. For example, a first colored region may indicate a shallow depth of penetration and thereby simultaneously indicate healthy teeth. A second, or more, colored regions positioned above the first colored region would indicate deeper depths of penetration and, thereby, simultaneously indicate more serious periodontal conditions.

The periodontal probe tip of the present invention preferably incorporates a number of graduations which divide the probing end into specified increments. These graduations would also preferably be placed among the previously discussed color-coded regions and, thereby, provide a second, more accurate means available to the dentist for determining the precise measurement of gingival pocket-depths between a patient's teeth and gums. This would allow the dentist to record an accurate depth measurement of a pocket around a particular tooth so that the tooth could be later re-assessed to determine the success of remedial measures applied to the tooth.

An external or internal light source is intended to be coupled to the periodontal probe tip for purposes of supplying light to a patient's mouth. A dental tool or a custom handle incorporating a light source would suffice in this function. The light conducting, translucent plastic of the probing end transmits light from the light source to the color-coded regions and graduations placed upon the probing end, thereby allowing a user to obtain accurate diagnostic measurements. Additionally, the probe tip incorporates a light bar, which is also constructed from translucent, light-conducting plastic, for purposes of supplying an additional source of illumination for illuminating an examination point within a patient's mouth.

The present invention preferably includes a probing ball coupled to the probing end, thus providing a blunt surface for contacting a subject patient's gum tissue. This feature allows the probing end of the probe tip to contact the bottom region of a patient's gingival pocket, known as the sulcus, with substantial pressure, without puncturing the sulcus and, thus cause the probing end to drive deeper and result in a false depth reading. Also, preferably, the probe tip is detachably coupled to the handle or dental tool which serves both as a light source and as a means for articulating the probe tip inside a patient's mouth. The detachability feature allows the present invention to be removed from the handle or dental tool for purposes of autoclaving or for purposes of replacement, thus reducing the likelihood of transmitting communicable diseases, such as AIDS or hepatitis.

An object of the invention is to provide a periodontal probe tip which can be illuminated for obtaining easily read, accurate, measurements of gingival pocket depths.

Another object of the invention is to provide a periodontal probe tip which can be detachably coupled to a plurality of common dental tools incorporating light sources.

Another object of the invention is to provide a periodontal probe tip which can be used for readily determining the level of progression of periodontal disease within a subject patient's mouth.

Another object of the invention is to provide a periodontal probe tip which employs color-coding for generally determining a patient's periodontal health and measured graduations for more accurately determining the periodontal health of a patient.

Another object of the invention is to provide a periodontal probe tip which will not penetrate the sulcus of the gingival pocket of a patient undergoing a dental examination.

Another object of the invention is to provide a periodontal probe tip which allows the fleshy gum tissue of a patient to be transilluminated for purposes of characterizing the underlying bony architecture of the gums.

Another object of the invention is to provide a periodontal probe tip which conforms to the Periodontal Screening and Recording (PSR) system endorsed by the World Health Organization and recommended by the American Dental Association.

Another object of the invention is to provide a method for using the periodontal probe tip disclosed herein.

Still another object of the invention is to provide a periodontal probe tip which is detachable and disposable.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 is a side elevation view of the periodontal probe tip of the present invention.

FIG. 2 is a perspective view of the periodontal probe tip of the present invention shown attached to a light source in phantom.

FIG. 3 is an exploded view of the apparatus of FIG. 1 shown with a light source in phantom.

FIG. 4 is an assembled view of the apparatus shown in FIG. 3.

DESCRIPTION OF THE PREFERRED EMBODIMENTS

Figure 5:
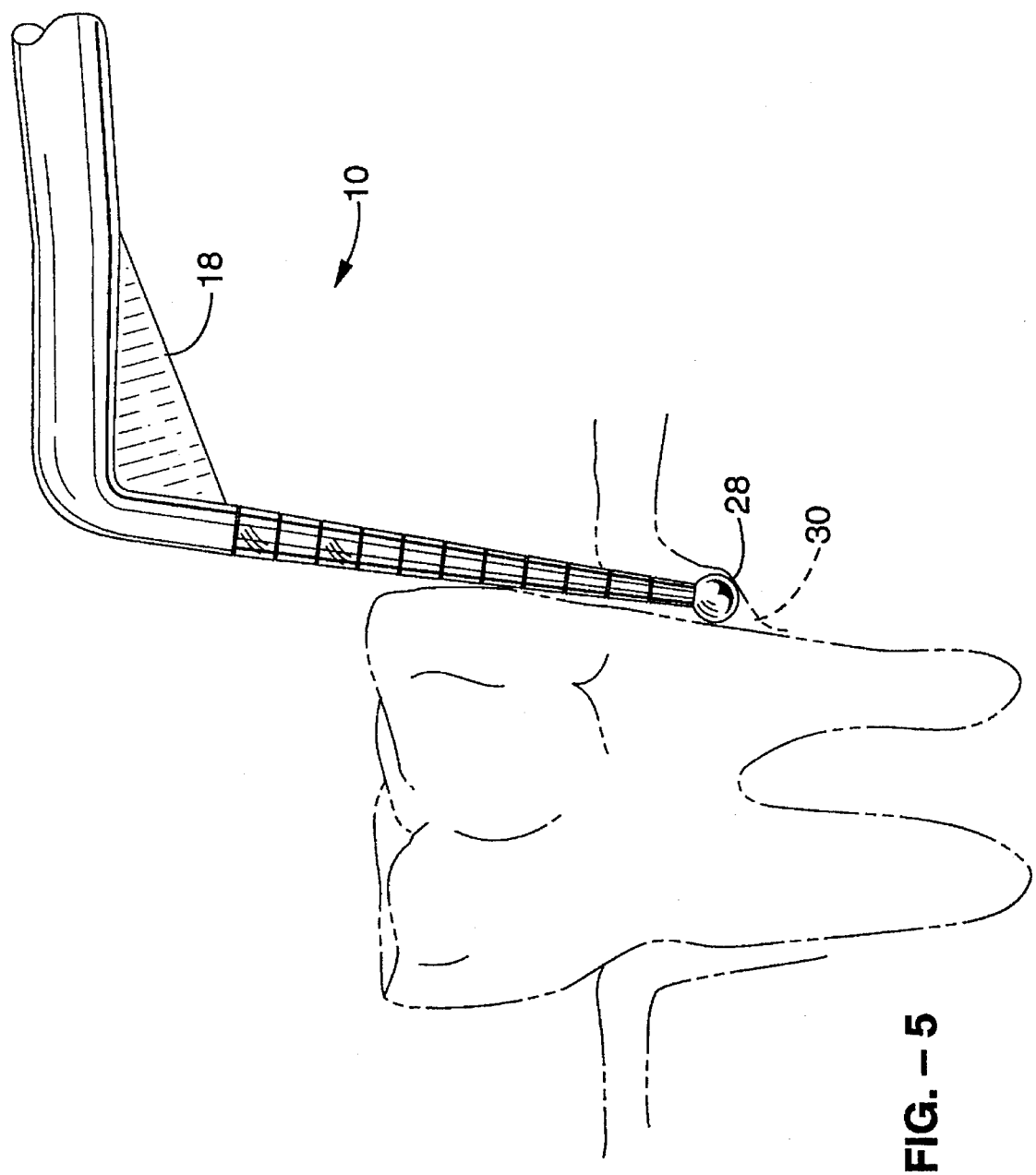
FIG. 5 is a diagrammatic view of the probing end of the present invention inserted at the juncture between a healthy tooth and gum.
Figure 6:
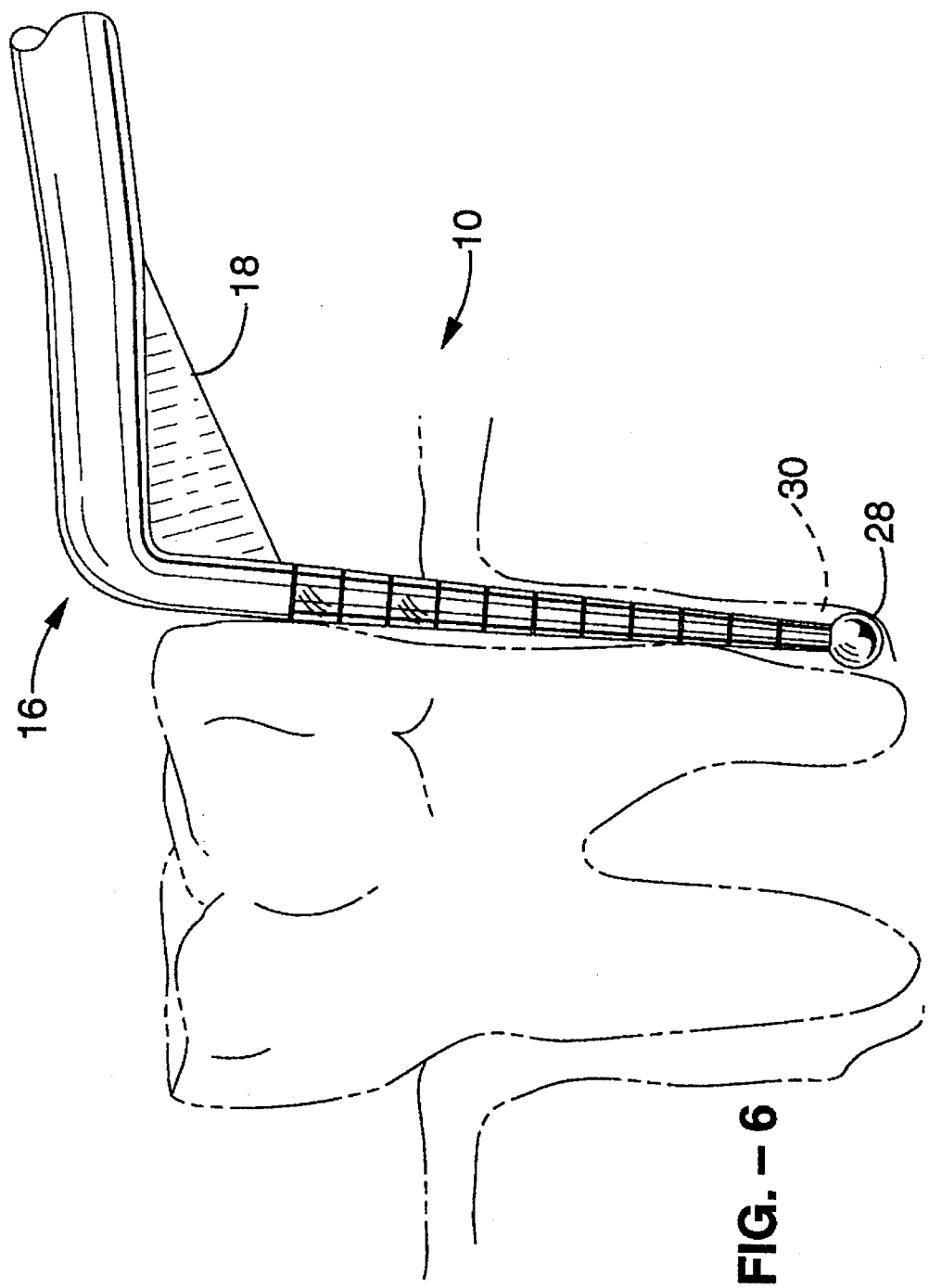
FIG. 6 is a diagrammatic view of the probing end of the perspective view of the periodontal probe tip of the present invention inserted at the juncture between a diseased tooth and gum.

Referring more specifically to the drawings, for illustrative purposes, the present invention is embodied in the periodontal probe tip 10 generally shown in FIG. 1 through 6 and the method of use described herein. It will be appreciated that probe tip 10 may vary as to configuration and as to details of the parts, and that the method of use may vary as to the steps and their sequence, without departing from the basic concepts as disclosed herein.

Referring to FIG. 1 and FIG. 2, a periodontal probe tip 10 in accordance with the present invention is shown. Probe tip 10 has a proximal attachment end 12 and a distal probing end 14. Distal probing end 14 is disposed in an angular relation to proximal attachment end 12, wherein curve 16 divides the two ends 12 and 14. Light bar 18 is disposed upon the interior radial portion of curve 16 between attachment end 12 and probing end 14. In the preferred embodiment, proximal attachment end 12 includes a coupling means 20 for detachably coupling to a light source 22. Light source 22 may be selected from a plurality of dental tools which incorporate a lighting means, or else a custom manufactured handle having a lighting means. Distal probing end 14 of probe tip 10 includes a plurality of adjacent colored regions 24a, 24b, and 24c which serve as primary indicators of periodontal disease, wherein each color represents differing levels of progression of periodontal disease. Colored regions 24a, 24b, 24c may be represented by differing shades of a similar color, however, it has been found to be preferable that the colored regions be represented by differing colors. For example, region 24a may be green, region 24b may be yellow and region 24c may be red, wherein green indicates healthy teeth, yellow indicates marginally healthy teeth and red would indicate unhealthy teeth.

In the preferred embodiment, a plurality of graduations 26 are placed into probing end 14. Graduations 26 act as a secondary indicator for diagnosing periodontal disease. When in use, a dentist would first use the colored regions 24a, 24b, 24c as a primary indicator to generally diagnose the condition of a patient's teeth. Depending on whether a subject patient's teeth indicate green, yellow or red, the dentist would then examine graduations 26 as a secondary method for precisely measuring the depth of the gingival pockets between a patient's teeth and gums. The dentist could then record the gingival pocket depths of individual teeth to compare against future office visits where the same teeth are examined. By tracking the depth of gingival pockets between subsequent office visits, the dentist could determine the success of remedial procedures applied to a patient's teeth.

Graduations 26 preferably take the form of scored indentations upon probing end 14. Also, preferably, graduations 26 remain clear in color so as to allow for maximum light transmission. Additionally, it is preferable that graduations 26 be spaced at 1 mm intervals to provide measured bands, and it is envisioned that each 1 mm graduation would be conspicuously numbered in a consecutive manner. The colored regions 24a, 24b, 24c would preferably be separated into bands correspond to the following measurement sequence: green—2 and 3 mm; yellow—4, 5 and 6 mm; and red—7, 8 and 9 mm. Additionally, probe tip 10 preferably has a supplemental region 24d having alternating clear and colored bands, which spans beyond the red colored region 24c and provides coding for 10, 11, and 12 mm.

At the endmost point of distal probing end 14 is coupled probing ball 28. Probing ball 28 serves as a blunt surface for contacting tissue at the bottom of gingival pockets. The blunt character of probing ball 28 prevents probing end 14 from puncturing the tissue at the bottom of gingival pockets. Probing ball 28 preferably provides the first 1 mm of probing end 14 and is preferably clear in coloration for purposes of more effectively transmitting light. Alternatively, probing ball 28 could be 0.5 mm in diameter, in which case the first green band would be either 0.5 mm or 1.50 mm in length. As can be seen, therefore, the distal end of probing ball 28 is the reference point from which all of the millimeter measurements are made.

Referring also to FIG. 3, FIG. 4, FIG. 5, and FIG. 6, it can be seen that periodontal probe tip 10 is capable of being illuminated for allowing a dentist to easily read colored regions 24a, 24b, 24c and graduations 26, upon probing end 14. While probe tip 10 may be completely translucent, it has been found to be preferable if proximal attachment end 12 is constructed from a non-translucent plastic-like material which is non-illuminating while distal probing end 14 is constructed from a clear, translucent, plastic-like material capable of conducting and emitting light. By constructing probe tip 10 in this way, the non-illuminating proximal attachment end 12 is able to effectively channel light from light source 22 into distal probing end 14 where it is needed, without dissipating the light as it travels. Light bar 18, is also constructed from a clear, translucent, light-emitting plastic-like material. An additional characteristic of the plastic-like material incorporated into probing end 14 is that it should have an appropriate flex modulus for allowing probing end 14 to flex, upon being applied against the bottom of gingival pocket 30, thus avoiding puncturing gingival pocket 30.

Light source 22 for illuminating periodontal probe tip 10 may be an external or internal light source 22. In the preferred embodiment, light source 22 is derived externally from a dental tool such as a lighted dental camera, a light wand, or a lighted dental drill. Probe tip 10, by being able to utilize existing dental tools as light sources 22, obviates the necessity for a dentist to purchase an additional tool to serve as a light source 22. Additionally, light source 22 may be a custom-manufactured light source 22 designed specifically for use with probe tip 10. Light source 22 would additionally serve as a handle for articulating probe tip 10 within a subject patient's mouth.

Preferably, light source 22 would detachably couple to probe tip 10 by a detachable coupling means 20. Detachable coupling means 20 may be represented by any one of a plurality of means for coupling probe tip 10 to light source 22, and the type of coupling means 20 used is strictly dependent upon the light source 22 employed. For purposes of illustration and not of limitation, coupling means 20 may be a clip, a slide-adaptor, a screw-type adaptor, etc. Moreover, coupling means 20 may be separate from probe tip 10 or else incorporated directly into the structure of probe tip 10 as a one-piece unit.

Additionally, probe tip 10 may be coupled to a dental camera by use of an appropriate coupling means 20. The transillumination of gingival pocket 30 as well as the light emitted from light bar 18 would provide sufficient illumination for the use of a dental camera, thus allowing a dentist to visually record an examination for diagnostic purposes, or else for illustrating to the patient, first-hand, the condition of his/her teeth and gums.

Upon coupling probe tip 10 to light source 22, light bar 18 and probing ball 28 exist as the two sources of brightest illumination upon probe tip 10. Preferably, probing ball 28 and light bar 18 would remain clear in coloration so that maximal light transmission is achieved. Light bar 18 preferably has a substantially rectangular bottom surface which serves as a light emitting surface for training light on areas of the mouth undergoing examination. Light bar 18 also provides structural integrity and reinforces the area of probe tip 10 surrounding curve 16 in addition to providing a light-emitting function.

Colored regions 24a, 24b, 24c transmit less light than light bar 18 and probing ball 28, due to the preferably opaque character of the coloration used to impregnate the translucent plastic-like material of colored regions 24a, 24b, 24c. The amount of light emitted from colored regions 24a, 24b, 24c would still be substantial enough to give the dentist a clear indication of the colors present upon probing end 14 so that an accurate diagnosis of a patient's teeth and gums can be made. The light emitted from probe tip 10 is a "cool" light, which remains at a low temperature, so that a patient does not experience discomfort and so any tissue surrounding probe tip 10 remains undamaged.

Upon placing probing end 14 within gingival pocket 30, the bright illumination of probing ball 28 would result in the transillumination of gingival pocket 30, such that the dentist may readily determine the size of pocket 30, by noting the depth to which the pocket is illuminated. In this way, the dentist may further determine the character of the bony architecture to which a patient's teeth are embedded and, thereby, judge the amount of bone loss suffered by the patient. Additionally, the illumination provided from probe tip 10 is useful for illuminating fistula tracts, endodontic access openings and other confined regions within the mouth.

By further reading the colored regions 24a, 24b, 24c which protrude from gingival pocket 30, the dentist may obtain the following quick initial indications of the health of the pocket: green indicating healthy, yellow indicating marginally healthy, and red indicating unhealthy teeth and gums. Graduations 26 serve as secondary indicators by which the dentist may obtain a precise measurement of a patient's gingival pockets 30. The clear coloration of graduations 26 allows them to stand out among colored regions 24a, 24b, 24c, thus allowing the dentist to easily count each increment and obtain a precise measurement. Additionally, probe tip 10 incorporates a supplemental region 24d positioned above red region 24c. Supplemental region 24d is preferably comprised of alternating clear and red increments, the clear increments allowing for the transmission of light, and the red increments indicating to the dentist the extreme deterioration of the patient's gingival pockets 30, should a patient be indicating in this region.

Referring to FIG. 4 and FIG. 5, the preferred method for using the periodontal probe tip 10 of the present invention can be more clearly described. In normal use, the dentist would retract the subject patient's lips and insert probing end 14 into the patient's gingival pockets 30. The dentist would advance probing end 14 into the patient's gingival pocket 30 until probing ball 28 contacts the bottom of pocket 30. At this point the dentist would first inspect the colored regions 24 a–c on the illuminated probe tip 10 to obtain a general indication of the depth of the patient's gingival pockets 30. If probe tip 10 reads green, the dentist would be assured that the pocket is healthy. Alternately, if probe tip 10 reads yellow or red, the dentist would have reason to suspect the health of the pocket 30 and would then move to the next step, which would be to use graduations 26 to measure the precise depth of gingival pocket 30. Upon reading the depth as indicated by the numbered graduations 26, the dentist would record this depth reading for diagnostic purposes. At the same time, the illuminated probing ball 28 would reveal the condition of gingival pocket 30 via transillumination. The transillumination of gingival pocket 30 would reveal the general size of the gingival pocket 30 and, thereby, the level of bone deterioration around the tooth, as well as the depth of advancement of the probing end 14 into gingival pocket 30. The dentist, would have the option of recording the condition of gingival pocket 30 by using a dental camera, the illumination of probe tip 10 and light bar 18 providing more than sufficient light for the camera recording procedure. The dentist would then withdraw periodontal probe tip 10 and repeat the above procedure a second time, on the same tooth, for purposes of confirming the first diagnosis. Subsequent to repeating the above-described procedure, the dentist would move to a second tooth to practice the method upon.

Accordingly, it will be seen that this invention provides a periodontal probe tip 10 having numerous features for quickly diagnosing the periodontal health of subject patients. Additionally, the present invention provides a method for using the periodontal probe tip 10 disclosed herein, for achieving maximum efficiency in diagnosing periodontal disease.

Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. A dental probe tip for diagnosing periodontal disease, comprising:
   (a) attachment means for coupling to a source of light;
   (b) probing means, joined to said attachment means, for being illuminated by said source of light and for determining the depth of a periodontal pocket;
   (c) said probing means including color indicator means for being illuminated by said source of light and for providing a relative indication of degree of periodontal disease;
   (d) said probing means including an illuminating probing ball; and
   (e) said color indicator means including a plurality of colored bands separated by translucent graduations into measured increments of predetermined length.

2. An apparatus as recited in claim 1, wherein said color bands are arranged in the following sequence:
   (a) a red band positioned closest to said attachment means;
   (b) a green band positioned closest to said probing ball; and
   (c) a yellow band positioned between said green band and said red band.

3. An apparatus as recited in claim 2, further comprising a supplemental region having alternating clear and colored bands separated by translucent graduations into measured increments of length, said supplemental region positioned adjacent to said red band and toward said attachment means.

4. An apparatus as recited in claim 1, wherein said graduations are spaced at 1 mm increments.

5. An apparatus as recited in claim 1, further comprising coupling means for detachably coupling said attachment means to said light source.

6. An apparatus as recited in claim 1, further comprising a light bar, said light bar positioned adjacent to said attachment means and said probing means.

7. A disposable tip for a periodontal probe, comprising:
   (a) a curved member, said curved member having an attachment means for coupling to a source of light;
   (b) said curved member having a probing means joined to said attachment means for being illuminated by said source of light, said probing means being translucent in appearance, said attachment means being non-translucent in appearance, said probing means further including adjacent, color-coded regions;
   (c) said probing means further including graduations placed thereon, said graduations dividing said color-coded regions into measured increments;
   (d) said probing means further including a probing ball coupled thereto;
   (e) said illumination of said probing means resulting in said graduations and said color-coded regions being visible to a viewer's unaided eye.

8. An apparatus as recited in claim 7, wherein said color-coded regions are arranged in the following sequence:
   (a) a red region positioned closest to said attachment means;
   (b) a green region positioned closest to said probing ball; and
   (c) a yellow region positioned between said green and said red regions.

9. An apparatus as recited in claim 8, further comprising a supplemental region having both clear and colored increments, said supplemental region positioned adjacent to said red region and toward said attachment means.

10. An apparatus as recited in claim 9, wherein said graduations divide said probing means into 1 mm increments.

11. An apparatus as recited in claim 10, further comprising coupling means for detachably coupling said attachment means to said source of light.

12. An apparatus as recited in claim 11, further comprising a light bar, said light bar positioned adjacent to said attachment means and said probing means.

13. A method for indicating periodontal disease, comprising the steps of:
   (a) illuminating a probing end of a dental probe, said probing end including a plurality of color coded bands and a plurality of graduations thereon, said probing end including a probing ball;
   (b) inserting said probing end of said dental probe into the juncture between a patient's tooth and periodontal tissue until said probing ball contacts the bottom of said patient's gingival pocket;
   (c) viewing said color coded bands to determine the extent of progression of periodontal disease; and
   (d) removing said probe end from between said tooth and said periodontal tissue.

14. A method as recited in claim 13, further comprising the step of viewing said graduations to determine the depth of said periodontal pocket.

15. A method for indicating periodontal disease, comprising the steps of:
   (a) providing an illuminating dental probe, said probe having an translucent probing end, said probing end including a plurality of color-coded bands separated by a plurality of graduations, said probing end including a probing ball;
   (b) retracting the lip of a patient to be diagnosed;
   (c) inserting said translucent probing end of said illuminating dental probe into the juncture between said patient's teeth and gums until said probing ball contacts the bottom of said patient's gingival pocket;
   (d) reading said color coded bands on said probing end to determine the extent of progression of periodontal disease; and
   (e) reading said graduations on said probing end, if said color coded bands indicate substantial progression of periodontal disease.

* * * * *